United States Patent [19]

Mendiratta

[11] 4,293,721

[45] Oct. 6, 1981

[54] PROCESS FOR THE PURIFICATION OF ALKALINE SOLUTION OF LOWER ALKYL ALCOHOLS CONTAINING ALKALI METAL ALKOXIDES

[75] Inventor: Sudhir K. Mendiratta, Cleveland, Tenn.

[73] Assignee: Olin Corporation, New Haven, Conn.

[21] Appl. No.: 175,175

[22] Filed: Aug. 4, 1980

[51] Int. Cl.³ .................. C07C 29/76; C07C 29/88
[52] U.S. Cl. .................................. 568/916; 568/913
[58] Field of Search ...................... 568/917, 916, 913

[56] References Cited

U.S. PATENT DOCUMENTS

| | | | |
|---|---|---|---|
| 1,824,610 | 9/1931 | Lyford | 568/913 |
| 2,463,000 | 3/1949 | Sevon | 568/913 |
| 2,608,589 | 8/1952 | Anglaret | 568/913 |
| 2,662,100 | 12/1953 | Hill | 568/851 |
| 2,882,243 | 4/1959 | Milton | 568/917 |
| 2,882,244 | 4/1959 | Milton | 568/917 |
| 3,082,260 | 3/1963 | Tedeschi et al. | 568/916 |
| 3,208,987 | 9/1965 | Reid et al. | 568/913 |
| 3,479,381 | 11/1969 | Mitchell | 568/916 |
| 3,600,449 | 8/1971 | Dombro | 568/913 |

FOREIGN PATENT DOCUMENTS 240694 12/1969 U.S.S.R. .................. 568/916

Primary Examiner—Joseph E. Evans
Attorney, Agent, or Firm—James B. Haglind; Donald F. Clements

[57] ABSTRACT

A novel process for purifying an alkaline solution of a lower alkyl alcohol containing as an impurity an alkali metal alkoxide, an alkali metal hydroxide, and water is disclosed. The process comprises treating the alkaline solution of a lower alkyl alcohol with an anhydrous hydrogen halide to react with the alkali metal alkoxide and the alkali metal hydroxide to provide a neutral solution comprised of the lower alkyl alcohol, an alkali metal halide and water. The alkali metal halide is removed from the neutral solution to obtain a substantially salt-free solution comprised of the lower alkyl alcohol and water. A zeolite molecular sieve is contacted with the solution to remove the water and to recover a substantially anhydrous solution of a lower alkyl alcohol. The process produces purified substantially anhydrous alcohol solutions suitable for the use in the production of alkali metal alkoxides such as sodium methoxide without introducing undesired amounts of alkaline impurities into the product.

14 Claims, No Drawings

PROCESS FOR THE PURIFICATION OF ALKALINE SOLUTION OF LOWER ALKYL ALCOHOLS CONTAINING ALKALI METAL ALKOXIDES

This invention relates to the purification of alcohols. More particularly, this invention is related to the removal of alkaline impurities and water from lower alkyl alcohols.

In the production of metal alkoxides such as alkali metal alkoxides by the reaction of an alkali metal or alkali metal compound with an alcohol, solutions of the alcohol are recovered which contain as undesired impurities alkali metal compounds and water. Before re-using these impure alcohol solutions in the metal alkoxide process, it is necessary to remove impurities such as alkali metal alcoholates, alkali metal hydroxides and water to prevent undesired dilution and contamination of the product.

The removal of hydroxides from alcohol solutions of alcoholates by treating the solution with silicon or a metal silicide as described in U.S. Pat. No. 2,662,100 issued to E. F. Hill. This process, however, does not eliminate alkali metal alkoxide impurities and may introduce silicon-containing impurities into the alcohol solution.

There is a need for a process for removing alkali metal alkoxides from an alcohol solution.

It is an object of the present invention to provide a process for purifying lower alkyl alcohols which effectively reduces the concentration of alkali metal compound impurities.

Another object of the present invention is to provide a process for purifying lower alkyl alcohols in which the concentration of water is substantially reduced.

These and other objects of the present invention are accomplished in a process for purifying alkaline solutions of lower alkyl alcohols containing as impurities alkali metal alkoxides and alkali metal hydroxides which comprises:

(a) treating the alkaline solutions of lower alkyl alcohols with an anhydrous halogen halide to react with the alkali metal alkoxides and alkali metal hydroxides to provide neutral solutions comprised of the lower alkyl alcohols, an alkali metal halide and water;

(b) removing the alkali metal halide from the neutral solution to obtain a substantially salt-free solutions comprised of the lower alkyl alcohols and water; and (c) contacting the substantially salt-free solutions with a zeolite molecular sieve to remove the water and recover substantially anhydrous solutions of the lower alkyl alcohols.

More in detail, the novel process of the present invention treats alkaline solutions of lower alcohols which contain as impurities alkali metal alkoxides, alkali metal hydroxides and water. Suitable lower alkyl alcohols are those having from 1 to about 4 carbon atoms in the alkyl group, for example, methanol, ethanol, propanol and tert-butanol, with methanol being a preferred embodiment. These alcohols contain varying amounts of alkali metal alkoxides, alkali metal hydroxides and water, which must be substantially removed if the alcohol is to be re-used, for example, in the production of alkali metal alkoxides. The alkali metal compounds present as impurities make the alcohol solutions highly alkaline, the pH of the solution being, for example, in the range of from about 9 to about 13.5. The alkoxide group will normally be the same as the alkyl group and will include alkoxides having from 1 to about 4 carbon atoms such as methoxide, ethoxide, propoxide and tert-butoxide. Any alkali metal may be present in the alkali metal alkoxides and alkali metal hydroxides, for example, sodium, lithium or potassium, with sodium more commonly being the alkali metal impurity.

In order to simplify the disclosure, it will be described in terms of alkaline methanol solutions containing as impurities sodium methylate, and sodium hydroxide, however, one skilled in the art will recognize that it will apply to alkaline solutions of the alkoxides discussed above. Sodium methylate is present in the alkaline methanol solutions in concentrations of from about 0.05 to about 25, and normally from about 0.1 to about 5 percent by weight. The concentration of sodium hydroxide is from about 0.05 to about 15, and usually from about 0.1 to about 5 percent by weight, with methanol comprising the balance of the solution.

To remove the alkali metal compound impurities, the alcohol solution is treated with an anhydrous halogen halide, for example, hydrogen chloride or hydrogen bromide with hydrogen chloride being preferred. Sufficient amounts of the anhydrous halogen halide are added to completely react with the sodium methylate and sodium hydroxide present. Where anhydrous hydrogen chloride is employed, the reactions are believed to take place according to the following equations:

$$NaOCH_3 + HCl \rightarrow NaCl + CH_3OH \qquad (1)$$

$$NaOH + HCl \rightarrow NaCl + H_2O \qquad (2)$$

As shown, sodium chloride is produced in both reactions, the addition of hydrogen chloride being continued until the alcohol solution is substantially neutral, having a pH of about 7.0. Reaction conditions such as temperature and pressure are not critical as the reaction readily takes place at temperatures in the range of from about 0° to about 60° C. at atmospheric pressure. However, higher or lower pressures may be employed if desired. The anhydrous hydrogen chloride gas may be fed to the reaction mixture directly or, preferably, it is admixed with a carrier gas such as nitrogen, helium, or other inert gases and the gaseous mixture fed into the alkaline solution.

The neutral solution obtained by the treatment of the alkaline solution with hydrogen chloride contains undesired amounts of sodium chloride. To remove substantially all of the sodium chloride, the solution may be, for example, distilled and a substantially salt-free solution of methanol and water recovered. Where the sodium chloride is present as solid crystals, it is advantageous to separate the solid salt from the neutral solution, for example, by filtering or centrifuging before removing the dissolved sodium chloride.

Distillation of neutral solutions of methanol containing dissolved sodium chloride concentrations in the range of about 1.0 to about 1.5 percent by weight of NaCl is accomplished at temperatures in the range of from about 60° to about 75° C. and at pressures of from about 25 to about 760 millimeters of Hg. The substantially salt-free solution of methanol and water contains less than about 2 parts per million of sodium chloride.

Water is removed from the substantially salt-free solution by passing the solution through a zeolite adsorbent such as natural or synthetic molecular sieves. Included amount these are such natural zeolitic molecular sieves as chabazite, faujasite, erionite, mordenite and gmelinite and such synthetic zeolitic molecular sieves as types A, X, and Y. Zeolites possess the characteristic of being able to undergo dehydration with little, if any change in crystal structure.

Preferred synthetic zeolitic molecular sieves are the type A zeolites, and particularly, types 3A and 4A in which the numbers correspond approximately to the nominal pore size openings in angstrom units. Type 3A and 4A sieves are dehydrated potassium and sodium zeolites, respectively, the zeolites having the same crystalline structure and being readily interchangeable by simple basic change procedures. Type A zeolites are represented by the following approximate empirical formula:

$$M_{2/v}O \cdot Al_2O_3 \cdot 2SiO_2 \cdot YH_2O$$

wherein M represents a metal in Groups I, II of the periodic table such as potassium, sodium, calcium, and strontium; transition metals of the periodic table such as nickel; hydrogen or ammonium; v represents the value of M and Y may be any value between 1-6 depending on the nature of M. The transition metals are those whose atomic numbers are from 21-28, from 39-46 and from 72-78 inclusive. Thus, for example, the empirical formula for type 3A zeolite is $Na_2O \cdot Al_2O_3 \cdot 2SiO_2 \cdot 4.5 H_2O$.

Synthetic zeolitic molecular sieves of type X and Y are truncated octahedra, with access to the inner cavity by four 12-sided windows each having a diameter of about 8-9 angstroms.

Regardless of whether natural or synthetic zeolite material is employed, the particles of material utilized are preferably regular in shape and size and must be sufficiently hard or attrition-resistant that they do not wear away during use, regeneration or other handling. The zeolitic material is activated or regenerated by heating to effect the loss of the water of hydration. For efficiency and economy, dehydration at a temperature of 150°-320° C. is generally used. It might occasionally be necessary for the regeneration temperature to be taken above 320° C., but not above the thermal stability temperature of the material which is about 565° C. Above the latter temperature the essential crystalline structure will begin to suffer destruction.

Zeolite molecular sieves may be added to the substantially salt-free solution and admixed with agitation to remove the water present. It is preferred, however, to pass the methanol solution containing water through, for example, a column of the zeolite molecular sieves and recover a substantially anhydrous methanol solution containing less than about 6.0 and preferably less than about 2.0 grams per liter of $H_2O$. Any suitable flow rates may be employed in passing the substantially salt-free methanol solution containing water through the zeolite molecular sieves. Suitable flow rates include those in the range of from about 1 to about 30, and preferably from about 2 to about 12 bed volumes per hour.

In an alternate embodiment, the alkaline solutions of methanol are treated with small amounts of concentrated aqueous solutions of hydrochloric acid or hydrobromic acid. The sodium methoxide present is hydrolyzed to the alcohol and sodium hydroxide by the water present in the solution. The sodium hydroxide present in turn reacts with the acid to form a sodium chloride or bromide which, along with the water present, are removed by the methods described above.

The alkaline solutions of methanol, in another alternate embodiment, may be treated with sufficient amounts of water to hydrolyze the sodium methoxide present to form methanol and sodium hydroxide. An anhydrous hydrogen halide is added to the solution as described above to form sodium chloride which is removed by the methods described above.

The novel process of the present invention can also be employed to purify lower alkyl alcohol solutions containing an alkali metal alkoxide impurity in the absence of an alkali metal hydroxide. The alcohol solution may be treated, for example, with water to hydrolyze the alkoxide to the alcohol and an alkali metal hydroxide or reacted with an anhydrous hydrogen halide to convert the alkoxide to an alkali metal halide. Further purification is accomplished by one of the methods described above.

The purified, substantially anhydrous alcohol solutions obtained by the novel process of the present invention may be used, for example, in the production of alkali metal alkoxides such as sodium methoxide without introducing undesired amounts of alkaline impurities or water into the products.

The novel process of the present invention is further illustrated by the following examples without any intention of being limited thereby.

EXAMPLES 1-4

To a reaction vessel equipped with a pH probe and an agitator was added impure methanol solutions having a pH of 13-13.5 and containing varying amounts of sodium methylate and sodium hydroxide. A gaseous mixture of anhydrous hydrogen chloride in nitrogen was passed through the solution until the pH of the solution was about 7. Sodium methylate and sodium hydroxide in the methanol solution were completely converted to sodium chloride and water by reaction with the hydrogen chloride. Excess hydrogen chloride was fed to a scrubbing vessel. The amounts in the reactants and impurities are given in Table 1.

TABLE I

| | Purification of Methanol Solutions | | | | | |
|---|---|---|---|---|---|---|
| Ex. No. | Weight of MeOH Solution (Grams) | wt. % NaOCH₃ | wt. % NaOH | ppm NaCl | HCl Used (Grams) | NaCl Formed (Grams) |
| 1 | 1189.6 | .91 | 1.68 | 3.4 | 17.86 | 28.63 |
| 2 | 1204.2 | .35 | 2.11 | 1.8 | 18.45 | 29.57 |
| 3 | 1210.4 | 1.56 | 3.31 | 5.1 | 17.81 | 28.54 |
| 4 | 1212.1 | — | 1.15 | 22.4 | 17.33 | 27.78 |

EXAMPLE 5

Methanol (0.4 liter) containing 14,130 parts per million of dissolved sodium chloride was distilled at 69° C. under vacuum (100 millimeters) into a condenser cooled with dry ice. The methanol recovered contained 1.3 parts per million of NaCl.

EXAMPLES 6-13

Solutions of methanol (1 liter) containing varying amounts of water as an impurity were passed through columns containing synthetic zeolite molecular sieve type 3A (Union Carbide Corp.). The solutions, at ambient temperature, were fed to the columns at various flow rates and the water adsorbed from the solutions determined as well as the amount of water remaining in the methanol solution after passing through the column. The results are recorded in Table II below.

TABLE II

WATER REMOVAL FROM METHANOL SOLUTIONS USING TYPE 3A MOLECULAR SIEVES

| Ex. No.* | Initial $H_2O$ Concentration (gpl) | Methanol Solution Flow Rate (bed volumes/hr.) | Water Absorbed (grams). (gpl) | $H_2O$ In Recovered Methanol Solutions |
|---|---|---|---|---|
| 6 | 21.9 | 4.10 | 16.32 | 5.4 |
| 7 | 27.6 | 1.87 | 26.50 | 0.8 |
| 8 | 26.5 | 3.73 | 24.03 | 2.2 |
| 9 | 14.5 | 5.60 | 12.91 | 1.7 |
| 10 | 16.5 | 7.45 | 12.59 | 3.7 |
| 11 | 15.8 | 11.20 | 11.56 | 4.0 |
| 12 | 15.8 | 5.60 | 13.78 | 2.2 |
| 13 | 16.5 | 11.20 | 13.46 | 2.8 |

*Example 6, bed volume = 295 mls.
Examples 7-13, bed volume = 643 mls.

What is claimed is:

1. A process for purifying an alkaline solution of a lower alkyl alcohol containing as impurities an alkali metal alkoxide and an alkali metal hydroxide which comprises:
    (a) treating said alkaline solution of a lower alkyl alcohol with an anhydrous hydrogen halide to react with said alkali metal alkoxide and said alkali metal hydroxide to provide a neutral solution comprised of said lower alkyl alcohol, an alkali metal halide and water;
    (b) removing said alkali metal halide from said neutral solution to obtain a substantially salt-free solution comprised of said lower alkyl alcohol and water; and
    (c) contacting said substantially salt-free solution with a zeolite molecular sieve to remove said water and to recover a substantially anhydrous solution of said lower alkyl alcohol.

2. The process of claim 1 in which said lower alkyl alcohol contains from 1 to about 4 carbon atoms in the alkyl group.

3. The process of claim 2 in which the initial concentration of said alkali metal hydroxide is from about 0.05 to about 15 percent by weight.

4. The process of claim 3 in which the initial concentration of said alkali metal alkoxides is from about 0.05 to about 25 percent by weight.

5. The process of claim 4 in which said anhydrous halogen halide is selected from the group consisting of hydrogen chloride and hydrogen bromide.

6. The process of claim 5 in which said alkali metal halide is removed by distilling said neutral solution.

7. The process of claim 1 in which prior to step (a) said alkaline solution of a lower alkyl alcohol is treated with water to hydrolyze said alkali metal alkoxide to form a lower alkyl alcohol and an alkali metal hydroxide.

8. The process of claim 1 or claim 7 in which said zeolite is a synthetic molecular sieve selected from the group consisting of Type A, Type X and Type Y.

9. The process of claim 8 in which said lower alkyl alcohol is methanol, said alkali metal alkoxide is sodium methoxide and said alkali metal hydroxide is sodium hydroxide.

10. A process for purifying an alkaline solution of a lower alkyl alcohol containing as impurities an alkali metal alkoxide and an alkali metal hydroxide which comprises:
    (a) treating said alkaline solution with a concentrated aqueous solution of an acid selected from the group consisting of hydrochloric acid and hydrobromic acid to provide a neutral solution comprised of said lower alkyl solution, an alkali metal halide, and water;
    (b) removing said alkali metal halide from said neutral solution to obtain substantially salt-free solution comprised of said lower alkyl alcohol and water; and
    (c) contacting said substantially salt-free solution with a zeolite molecular sieve to remove said water and to recover a substantially anhydrous solution of said lower alkyl alcohol.

11. A process for purifying a solution of a lower alkyl alcohol containing as an impurity an alkali metal alkoxide which comprises:
    (a) treating said lower alcohol solution with water to hydrolyze said alkali metal alkoxide to form an alkaline solution of a lower alkyl alcohol and an alkali metal hydroxide;
    (b) reacting said alkaline solution with an anhydrous hydrogen halide to provide a neutral solution comprised of said lower alkyl alcohol, an alkali metal halide and water;
    (c) removing said alkali metal halide from said neutral solution to obtain a substantially salt-free solution comprised of said lower alkyl alcohol and water; and
    (d) contacting said substantially salt-free solution with a zeolite molecular sieve to remove said water and to recover a substantially anhydrous solution of said lower alkyl alcohol.

12. A process for purifying a solution of a lower alkyl alcohol containing as an impurity an alkali metal alkoxide which comprises:
    (a) treating said solution of a lower alkyl alcohol with an anhydrous hydrogen halide to react with said alkali metal alkoxide to provide a neutral solution comprised of said lower alkyl alcohol, an alkali metal halide and water;
    (b) removing said alkali metal halide from said neutral solution to obtain a substantially salt-free solution comprised of said lower alkyl alcohol and water; and
    (c) contacting said substantially salt-free solution with a zeolite molecular sieve to remove said water and to recover a substantially anhydrous solution of said lower alkyl alcohol.

13. The process of claim 1 or claim 10 or claim 11 or claim 12 in which solid alkali metal halide is removed by the filtration of said neutral solution.

14. The process of claim 13 in which dissolved alkali metal halide is removed by the distillation of said neutral solution.

* * * * *

UNITED STATES PATENT AND TRADEMARK OFFICE
CERTIFICATE OF CORRECTION

PATENT NO. : 4,293,721

DATED : October 6, 1981

INVENTOR(S) : Sudhir K. Mendiratta

It is certified that error appears in the above-identified patent and that said Letters Patent are hereby corrected as shown below:

In Column 1, line 49, delete "solutions" and insert --solution--.

In Column 3, line 2, delete "amount" and insert --among--.

In Column 3, line 18, delete "$M_{2/v}O.Al_2O_3.2SiO_2.YH_2O$" and insert --$M_{2/v}O \bullet Al_2O_3 \bullet 2SiO_2 \bullet YH_2O$--.

In Column 3, line 28, delete "$Na_2O.Al_2O_3.2SiO_2.4.5H_2O$" and insert --$Na_2O \bullet Al_2O_3 \bullet 2SiO_2 \bullet 4.5H_2O$--.

In Column 4, Table I, under "Purification of Methanol Solutions" and above "wt. % NaOCH$_3$" through "ppm NaCl" insert --Impurities in MeOH Solution".

In Column 5, Table II, under column entitled "Methanol Solution Flow Rate" after "(bed volumes/hr." insert --)--.

UNITED STATES PATENT AND TRADEMARK OFFICE
CERTIFICATE OF CORRECTION

PATENT NO. : 4,293,721

DATED : October 6, 1981

INVENTOR(S) : Sudhir K. Mendiratta

It is certified that error appears in the above-identified patent and that said Letters Patent are hereby corrected as shown below:

In Column 5, Table II, under column entitled "Water Absorbed (grams)" delete "(gpl)".

In Column 5, Table II, under column entitled "$H_2O$ In Recovered Methanol Solutions" insert --(gpl)--.

In Column 6, Claim 10, line 13, after "alkyl" delete "solution" and insert --alcohol--.

Signed and Sealed this

Sixth Day of April 1982

[SEAL]

Attest:

Attesting Officer

GERALD J. MOSSINGHOFF

Commissioner of Patents and Trademarks